(12) United States Patent
Ariotto et al.

(10) Patent No.: US 8,383,090 B2
(45) Date of Patent: Feb. 26, 2013

(54) CLEANSING COMPOSITION BASED ON OILY SUBSTANCES

(75) Inventors: Angelo Ariotto, Terruggia (IT); Fabrizio Guala, Trino (IT); Elisabetta Merlo, Trino (IT); Giovanni Villa, Paderno Dugnano (IT)

(73) Assignee: Zschimmer & Schwarz Italiana S.p.A., Tricerro, Vercelli (IT)

( * ) Notice: Subject to any disclaimer, the term of this patent is extended or adjusted under 35 U.S.C. 154(b) by 1852 days.

(21) Appl. No.: 10/566,030

(22) PCT Filed: Jul. 15, 2004

(86) PCT No.: PCT/EP2004/007889
§ 371 (c)(1),
(2), (4) Date: Jan. 17, 2006

(87) PCT Pub. No.: WO2005/013927
PCT Pub. Date: Feb. 17, 2005

(65) Prior Publication Data
US 2007/0110697 A1    May 17, 2007

(30) Foreign Application Priority Data
Jul. 17, 2003   (IT) ............................... TO2003A0555

(51) Int. Cl.
*A61K 8/30*     (2006.01)
*A61K 9/00*     (2006.01)
*A61K 8/02*     (2006.01)

(52) U.S. Cl. ...................... 424/70.22; 424/400; 424/401
(58) Field of Classification Search ............... 424/70.22, 424/400, 401
See application file for complete search history.

(56) References Cited

U.S. PATENT DOCUMENTS

| | | | |
|---|---|---|---|
| 4,371,548 A | | 2/1983 | Hermann et al. |
| 4,946,618 A | * | 8/1990 | Knochel et al. ............... 510/151 |
| 5,227,086 A | * | 7/1993 | Kacher et al. ................. 510/146 |
| 5,653,988 A | * | 8/1997 | Gerber et al. ................. 424/401 |
| 5,843,407 A | | 12/1998 | El-Nokaly et al. |
| 6,132,738 A | | 10/2000 | Lerg et al. |
| 6,162,775 A | * | 12/2000 | Methmanus-Spaltro ..... 510/130 |
| 6,620,773 B1 | * | 9/2003 | Stork et al. .................... 510/130 |
| 2003/0162687 A1 | | 8/2003 | Tobita et al. |

FOREIGN PATENT DOCUMENTS

| | | |
|---|---|---|
| DE | 29 43 202 A1 | 3/1981 |
| JP | 01 146816 | 6/1989 |
| JP | 2000 007537 | 1/2000 |
| WO | WO 9533025 A1 * | 12/1995 |
| WO | 98/09611 | 3/1998 |
| WO | 98/29094 | 7/1998 |
| WO | 03/039496 A1 | 5/2003 |

OTHER PUBLICATIONS

International Journal of Toxicology, 2001, 20 (Suppl. 1), 1-14.*

* cited by examiner

*Primary Examiner* — Abigail Fisher
(74) *Attorney, Agent, or Firm* — Merchant & Gould P.C.

(57) ABSTRACT

A cleansing composition based on oily substances, particularly for cleansing skin and/or hair and having excellent dermatological properties, is described. The composition is characterized in that it comprises one or more oily substances at a total concentration of between 10% and 90% by weight relative to the composition and one or more surfactants selected from the N-acylates of amino-acids, proteins, and peptides, in acid or neutralized form, at a total concentration within the range of between 2% and 80% by weight relative to the composition, and in that it is substantially anhydrous or has a water content no greater than 10% by weight.

4 Claims, No Drawings

CLEANSING COMPOSITION BASED ON OILY SUBSTANCES

BACKGROUND OF THE INVENTION

The present invention relates to a novel cleansing composition based on oily substances, particularly for cleansing skin and/or hair, which has excellent dermatological properties.

Skin and hair can be cleansed in various ways, even with water alone. However, the use of water alone may cause swelling of the horny layer and depletion of the water-soluble constituents of the NMF (Natural Moisturizing Factor), that is, the group of water-soluble substances which are responsible for correct skin hydration. Moreover, water alone cannot remove dirt of an oily nature or any residues of a lipid nature.

For cleansing skin and hair, it is therefore usual to use either formulations based on water and surfactants, that is, molecules which, by virtue of their amphiphilic structure, are capable of removing lipid substances and keep them in aqueous solution or suspension, or formulations based on oily substances which make use of the "similia similibus solvuntur" principle. By virtue of their oily nature, these substances are in fact capable of removing sebum and hydrophobic dirt without, however, removing the water-soluble hydrating components (NMF) of the skin. This is particularly desirable when the skin or hair are irritated or damaged by environmental conditions (for example, atmospheric conditions or pollution) or physiological conditions (for example, ageing or sensitive skin).

There are many oily substances which can be used for this purpose and they may be either natural or synthetic. Amongst these are substances which are fluid at ambient temperature (oils), pasty substances (butters, fats), and solid substances (waxes). From the chemical point of view, these substances can be classified as:

hydrocarbons (paraffinic or naphthenic) such as mineral oil, vaseline, paraffin, ozocerite, ceresin;

terpenic hydrocarbons such as squalane, squalene, pristane, hexaisoprene, polyisobutylene;

siloxanic polymers such as silicones and other heterolipids, including propoxylated alcohols;

triglyceric esters such as most vegetable and some animal oils and fats (groundnut oil, karite butter, safflower oil, coconut butter, palm butter, soya oil, sunflower oil, olive oil, rice-germ oil, sweet almond oil, sesame oil, cocoa butter, wheat-germ oil, grape-seed oil, etc.); lecithin, which is a phosphatidyl cholinic glyceride, falls within this group;

non-triglyceric esters such as lanolin, beeswax, spermaceti, carnauba wax, candelilla wax, the uropygial fat of aquatic birds, and a great many synthetic esters (isopropyl myristate, which is most often used, may be mentioned by way of example);

fatty acids produced by the hydrolysis of vegetable fats (stearic acid is mainly used) of or lanolin (lanolic acids);

fatty alcohols (for example, oleyl alcohol, cetyl alcohol) sterolic alcohols (for example, cholesterol), triterpenic alcohols (for example, lanosterol); many of these alcohols form part of the non-saponifiable fraction of vegetable lipids; the group also includes synthetic alcohols such as octyl dodecanol;

essential oils, for example, essential oil of rosemary, lavender, angelica, artemisia, valerian, basil, bergamot, citronella, lemon, myrrh, patchouli, rose, or cinnamon.

However, cleansing compositions which are based on oily substances pose considerable formulation problems which are due both to poor solubility in water and to low foaming capacity. These problems have been addressed in the prior art by the use of various surfactants capable of increasing the dispersibility of the oily substances in water, improving the rinsability of the composition, and/or increasing foam formation.

For example, patent application DE-A 29 43 202 describes the use of monoalkylamines or dialkylamines, monoalkanolamines or dialkanolamines and/or salts of alkyl/alkanolamines of fatty alcohol sulphates as surfactants.

U.S. Pat. No. 4,371,548 describes the use of a $C_8$-$C_{18}$ sulphated fatty alcohol, optionally ethoxylated, neutralized by one or more amines, in a mixture with a $C_8$-$C_{10}$ ethoxylated sulphated fatty alcohol of ammonium.

U.S. Pat. No. 5,653,988 describes the use of a mixture constituted by a fatty alcohol, optionally ethoxylated, neutralized with various amines (preferably MIPA), an ethoxylated fatty alcohol (preferably Laureth-4) and a mono/diethanol amide (preferably Cocamide DEA).

U.S. Pat. No. 6,132,738 also describes the use of TIPA Laureth Sulphate.

However, a further problem to be addressed in the formulation of cleansing compositions for skin and/or hair is that of the aggressiveness of the surfactant. In the cosmetics field, there is in fact a tendency to avoid the use of ingredients, particularly surfactants, which are irritating to skin and hair. This is even more desirable for compositions which are based on oily substances, the beneficial effects of which would be cancelled out by the presence of an aggressive surfactant in the composition. For this reason, the current tendency in the cosmetics field is to avoid the use of aggressive surfactants such as, for example, cocamide DEA—because of the possible formation of nitrosamines—and sulphated fatty alcohols, because of their aggressiveness and the dioxane content of the ethoxylated derivatives.

The present inventors have now found that the use of acylates of amino-acids, proteins and/or peptides as surfactants in the formulation of cleansing compositions based on oily substances, particularly for cleansing skin and/or hair, enables compositions having excellent dermatological properties to be produced. These compositions have in fact been found to be extremely gentle towards skin and/or hair.

Simply adding these surfactants to a conventional oily formulation can reduce its aggressiveness and increase its tolerability. These molecules may also have a corrosion-inhibiting effect on domestic pipes.

SUMMARY OF THE INVENTION

A subject of the present invention is therefore a cleansing composition, particularly for cleansing skin and/or hair, comprising one or more oily substances at a total concentration within the range of between 10% and 90% by weight relative to the composition, preferably between 30% and 70%, and a surfactant selected from N-acylates of amino-acids, proteins, and peptides, and mixtures thereof, at a total concentration within the range of between 2% and 80% by weight relative to the composition, said N-acylates of amino-acids, proteins, and peptides having formula (I):

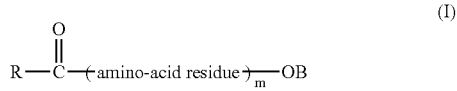

wherein:

R is a saturated or unsaturated, linear or branched radical with from 3 to 30 carbon atoms, and the acyl group R—CO— is bound by an amide bond to the amine-nitrogen of the amino-acid residue, m is a whole number ≧1, in which, when m>1, the repeated amino-acid residues may be identical to or different from one another, B is hydrogen or a cation of an inorganic or organic base, the composition being substantially anhydrous or having a water content no greater than 10% by weight.

In formula (I) above, the expression "amino-acid residue" includes both residues of non-cyclic amino-acids and residues of cyclic amino-acids. An amino-acid residue can be represented schematically by formula (II):

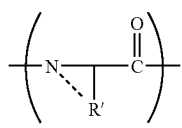

in which R' is the side chain of the amino-acid.

In the N-acylates of formula (I) which are used in the present invention, the acyl group R—CO— is bound to the amine-nitrogen of the amino-acid residue and the —OB group is bound to the carboxylic carbon of the amino-acid residue.

The N-acylates which are used in the present invention may be in acid form (when B═H) or may be neutralized (when B is a cation of an inorganic or organic base).

When B is a cation of an organic base, the organic base is preferably selected from MIPA (mono-isopropanol amine), TIPA (tri-isopropanol amine), Tris Amino (2-amino-2-hydroxymethyl-1, 3-propandiol), AEPD (2-amino-2-ethyl-1,3-propandiol), AMPD (aminomethyl propandiol) and AMP (aminomethyl propanol) Even more preferably, the organic base is AMP.

When B is a cation of an inorganic base, the inorganic base is preferably selected from KOH, NaOH and NH$_3$.

When, in formula (I), m is 1 (m=1), the surfactant is an N-acylate of an amino-acid. In this case, the amino-acid residue is preferably selected from the group consisting of the amino-acid residues of alanine, arginine, aspartic acid, asparagine, glutamic acid, glutamine, glycine, histidine, hydroxyproline, leucine, isoleucine, lysine, methionine, phenylalanine, proline, serine, threonine, tyrosine, valine, cystine, cysteine, sarcosine and pyrrolidone carboxylic acid.

When, in formula (I), m is greater than 1 (m>1), the surfactant is an N-acylate of a peptide or a protein. The peptides/proteins which are most preferred for this purpose are of vegetable origin (for example, rice, wheat, oats, maize, etc.) and are produced by the hydrolysis of the protein fraction of the plants used.

If other carboxylic groups are present on the side chains of the amino-acid residues, they may be in acid or salified form.

Surfactants which are particularly preferred for use in the composition of the invention are those in which the R—CO-acyl group is oleoyl or cocoyl. Most preferred amongst these are acid N-cocoyl sarcosinate and acid N-oleoyl sarcosinate, which can solubilize the oily substances contained in the composition, up to high concentrations, without the need for heating.

The surfactants which are used in the composition of the invention are synthesized by Schotten-Baumann reaction, starting with the chloride of the acid to be produced and with the desired amino-acid or peptide, or protein, in a basic NaOH or KOH environment. Upon completion of the reaction, acidification is then performed so as to obtain two phases, one constituted by the amino-acid or peptide or protein acylate in acid form and the other by water and sodium or potassium chloride (secondary reaction product). The acylate thus obtained can be used as such for the formulation of the cleansing composition or may be neutralized beforehand with a base as described above. Alternatively, the acylate in acid form may be added directly to the formulation and may then be neutralized subsequently in the formulation.

The use of the surfactants described above has been found to be extremely effective. These surfactants can in fact solubilize oily substances up to high concentrations (up to 90% by weight relative to the formulation), even without the need for heating, in the case of acid cocoyl and oleoyl sarcosinate. They also ensure optimal foaming and dermatological properties.

In some cases, to improve the clearness of the composition, it may be desirable to add an ethoxylated non-ionic surfactant, preferably an ethoxylated fatty alcohol.

In the cleansing composition of the invention, the above described N-acylates of amino-acids, peptides, or proteins can therefore be used individually or in mixtures. Their total concentration in the composition is within the range of from 2% to 80% by weight, preferably from 10% to 40% by weight, relative to the composition.

The cleansing composition of the invention may also optionally include further additives or active ingredients which are conventional for cosmetic compositions such as, for example, viscosifiers, colours, perfumes, antioxidants, and preservatives, the selection and correct use of which fall within the capabilities of a person skilled in the art and are therefore not described herein since they do not form a specific subject of the invention.

DETAILED DESCRIPTION OF THE INVENTION

The cleansing compositions of the invention are prepared in the following manner:

mixing together the oily substances to be used;

dissolving the appropriate fragrance (it is important that it does not give rise to cloudiness or incompatibility); if an ethoxylated non-ionic surfactant is used, dissolving the fragrance therein;

dissolving the desired surfactant/s and homogenizing to clearness;

optionally neutralizing the surfactant/s in acid form by the addition of a neutralizing base upon completion of the formulation.

Some examples of oily cleansing compositions according to the invention are given below. These examples are provided for illustrative purposes and are not intended in any way to limit the scope of the invention as defined in the appended claims.

EXAMPLES

Example 1

Bath Oil

| | |
|---|---|
| Acid oleoyl sarcosinate | 26% |
| Perfume | 1% |
| Soya oil | to 100% |
| Antioxidant | qds |

Example 2

Shower Oil

| | |
|---|---|
| Acid cocoyl sarcosinate | 10% |
| Perfume | 5% |
| Isopropyl palmitate | 15% |
| Paraffin oil | to 100% |

Example 3

Oily Face Wash

| | |
|---|---|
| Laureth-4 | 20% |
| Acid lauroyl glutamate | 20% |
| Olive oil | 48% |
| Isopropyl palmitate | 10% |
| Perfume | 2% |

Example 4

Shower Oil

| | |
|---|---|
| Cocoyl sarcosinate neutralized with AMP | 37% |
| Oleoyl sarcosinate neutralized with AMP | 30% |
| Wheat-germ oil | 3% |
| Vaseline oil FU (Farmacopea Ufficiale - Italian Official Pharmacopoeia) | 25% |
| Essence | 5% |
| Antioxidants | qds |

The invention claimed is:

1. A cleansing composition, comprising one or more oily substances at a total concentration within the range of between 30% and 70% by weight relative to the composition and a surfactant selected from the group consisting of acid N-cocoyl sarcosinate, acid N-oleoyl sarcosinate and mixtures thereof, at a total concentration within the range of between 10% and 40% by weight relative to the composition, the composition being anhydrous; wherein the composition is in the form of a liquid and suitable for cleansing skin and/or hair.

2. A cleansing composition according to claim 1, wherein the oily substance is selected from the group consisting of paraffinic hydrocarbons, naphthenic hydrocarbons, terpenic hydrocarbons, siloxanic polymers, triglyceric esters, non-triglyceric esters, fatty acids, fatty alcohols, essential oils, and mixtures thereof.

3. A cleansing composition according to claim 1, further comprising a non-ionic ethoxylated surfactant or a mixture of non-ionic ethoxylated surfactants.

4. A cleansing composition according to claim 3, wherein the non-ionic ethoxylated surfactant comprises an ethoxylated fatty alcohol.

\* \* \* \* \*